(12) United States Patent
Lee et al.

US011913923B2

(10) Patent No.: US 11,913,923 B2
(45) Date of Patent: Feb. 27, 2024

(54) METHOD FOR EVALUATING PROPERTIES OF MELT-BLOWN PLASTIC RESIN

(71) Applicant: LG Chem, Ltd., Seoul (KR)

(72) Inventors: Hyunsup Lee, Daejeon (KR); Seok Hwan Kim, Daejeon (KR); Heekwang Park, Daejeon (KR); Ki Soo Lee, Daejeon (KR); Sangjin Jeon, Daejeon (KR); Myunghan Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 18/127,457

(22) Filed: Mar. 28, 2023

(65) Prior Publication Data

US 2023/0236160 A1 Jul. 27, 2023

Related U.S. Application Data

(63) Continuation of application No. 16/645,298, filed as application No. PCT/KR2018/010633 on Sep. 11, 2018, now abandoned.

(30) Foreign Application Priority Data

Sep. 15, 2017 (KR) .......................... 10-2017-0118860

(51) Int. Cl.
G01N 30/88 (2006.01)
G01N 33/44 (2006.01)
G01N 30/02 (2006.01)

(52) U.S. Cl.
CPC ........... *G01N 30/88* (2013.01); *G01N 33/442* (2013.01); *G01N 2030/027* (2013.01)

(58) Field of Classification Search
None
See application file for complete search history.

(56) References Cited

U.S. PATENT DOCUMENTS

| 5,582,903 | A | 12/1996 | Levy et al. | |
|---|---|---|---|---|
| 9,211,688 | B1 | 12/2015 | Jeung et al. | |
| 2007/0112160 | A1 | 5/2007 | Schramm et al. | |
| 2007/0197716 | A1 | 8/2007 | Krishnaswamy et al. | |
| 2008/0199673 | A1 | 8/2008 | Allgeuer et al. | |
| 2010/0201041 | A1 | 8/2010 | Brandner et al. | |
| 2011/0184128 | A1 | 7/2011 | Guo et al. | |
| 2012/0316311 | A1* | 12/2012 | Yang ..................... | C08F 210/16 526/348.2 |
| 2013/0266874 | A1 | 10/2013 | Matsubara et al. | |
| 2016/0040335 | A1 | 2/2016 | Matsubara et al. | |
| 2017/0081444 | A1 | 3/2017 | Wang et al. | |
| 2018/0030194 | A1* | 2/2018 | Uehara ..................... | C08F 8/04 |

FOREIGN PATENT DOCUMENTS

| CA | 2975863 A1 | 8/2016 |
|---|---|---|
| CN | 1090899 A | 8/1994 |
| CN | 1959683 A | 5/2007 |
| CN | 100406849 C | 7/2008 |
| CN | 101230161 A | 7/2008 |
| CN | 101415768 A | 4/2009 |
| CN | 101495208 A | 7/2009 |
| CN | 101498079 A | 8/2009 |
| CN | 101613526 A | 12/2009 |
| CN | 102799742 A | 11/2012 |
| CN | 104626510 A | 5/2015 |
| CN | 106048887 A | 10/2016 |
| EP | 2650419 B9 | 3/2017 |
| JP | H1150375 A | 2/1999 |
| JP | 2016180660 A | 10/2016 |
| KR | 20080038230 A | 5/2008 |
| KR | 20080114740 A | 12/2008 |
| KR | 20140033083 A | 3/2014 |
| KR | 20150069039 A | 6/2015 |
| KR | 20170023078 A | 3/2017 |
| KR | 20170029239 A | 3/2017 |
| WO | 2016125899 A1 | 8/2016 |

OTHER PUBLICATIONS

Han, Jong-Hun et al., "Effect of Processing Factors on the Properties of Melt-blown PP/Ba-ferrite Composite Fabrics" J. Korean Ind. Eng. Chem., vol. 17, No. 3, Jun. 2006, pp. 267-273.
Lee JS, Lee M, Lim TY, Lee Y, Jeon DW, Hyun SK, Kim JH. Physical Properties of AR-Glass Fibers in Continuous Fiber Spinning Conditions. Korean Journal of Metals and Materials. Apr. 6, 2017;55(4):290-5.
Shim H. Effect of Processing Factors on the Physical Properties of Meltblown Polypropylene Fiberweb Fabrics (II)—Effects of Processing Factors on the Characteristics of the Constituent Fibers. Journal-Korean Fiber Society. Feb. 5, 1996;vol. 33, No. 6: pp. 492-498.
International Search Report for PCT/KR2018/010633 dated Jan. 24, 2019.
Extended European Search Report including Written Opinion for Application No. EP18855706.0, dated Oct. 27, 2020, pp. 1-5.
Tang, et al., Melt-blown Lyocell: Influence of Solution Characteristics on Fibre Properties, The Journal of the Textile Institute, 2006, vol. 97, No. 1, pp. 39-47, XP001240251, ISSN: 0040-5000. DOI:10. 1533/JOTI.2005.0211.
Liu, J. et al., "Effect of Molecular Weight on Stretched Polypropylene Microporous Membranes" Polymer Materials Science and Engineering, Feb. 2011, pp. 64-67, vol. 27, No. 2.
Xiubao, H. "Study on the Air Drawing in Melt Blowing Nonwoven Process" Dong Hua University, Doctoral Dissertation, Dec. 2003, pp. 1-125.

(Continued)

*Primary Examiner* — Harshad R Patel
*Assistant Examiner* — Gedeon M Kidanu
(74) *Attorney, Agent, or Firm* — Lerner David LLP

(57) ABSTRACT

A method for evaluating physical properties of a melt-blown plastic resin, and, more specifically, to a novel method for evaluating physical properties are provided. When a particular plastic resin is processed by a melt-blown process, a stretching diameter value after the process of the plastic resin can be accurately derived from a physical property value measured using a specimen of the resin.

9 Claims, No Drawings

(56) References Cited

OTHER PUBLICATIONS

Li, C. et al., "Preparation of Fiber Nonwovens Fabrics by Solution-Blown" Polymer Materials Science and Engineering, Feb. 2015, pp. 165-170, vol. 31, No. 2.
Choi, K.J. et al., "Strength Properties of Melt Blown Nonwoven Webs" Polymer Engineering and Science, Jan. 1988, pp. 81-89, vol. 28, No. 2.

* cited by examiner

METHOD FOR EVALUATING PROPERTIES OF MELT-BLOWN PLASTIC RESIN

CROSS-REFERENCE TO RELATED APPLICATION(S)

The present application is a continuation application of U.S. application Ser. No. 16/645,298 filed on Nov. 16, 2020, a national phase entry under 35 U.S.C. § 371 of International Application No. PCT/KR2018/010633 filed on Sep. 11, 2018, which claims priority from Korean Patent Application No. 10-2017-0118860 filed on Sep. 15, 2017, all the disclosures of which are incorporated herein by reference.

TECHNICAL FIELD

The present invention relates to a method for evaluating physical properties of a melt-blown plastic resin. More specifically, the present invention relates to a method for evaluating physical properties in which, when a particular plastic resin is processed by a melt-blown process, a stretching diameter value after the melt-blown process can be accurately derived from a physical property value measured using a specimen of the resin.

BACKGROUND ART

Nonwoven fabric or nonwoven web is a three-dimensional fiber aggregate in which fine fibers having a diameter of about 10 μm are randomly entangled to have a structure like a spider web.

Since the nonwoven fabric or the nonwoven web is formed by bonding fine fibers to each other, the nonwoven fabric or the nonwoven web is very excellent in texture, touch, or the like, and has good processability and excellent strength, ductility, and abrasion resistance.

Such nonwoven fabric is used for various purposes in various technical fields, such as bandage materials, oil absorbing materials, building materials for sound absorption, disposable diapers, feminine hygiene products or the like. In recent years, it is widely used also in the latest technology fields, such as dustproof clothing, a dustproof mask, a wiping cloth, a microfiltration filter, and a battery separator.

There are known several types of processes for producing a nonwoven fabric or a nonwoven web, but among them, a melt-blown process is most frequently used. The melt-blown process is a process in which the thermoplastic resin capable of forming a fiber yarn is discharged in a molten form through an orifice die to which a plurality of orifices having hundreds to thousands of cavities are connected, a high-temperature gas is injected from high-speed gas nozzles disposed on both sides of the die, fiber yarns are stretched into ultrafine yarns, and the ultrafine fiber yarns are laminated on the collection drum.

Such melt blown nonwoven fabrics can be used in various applications as described above due to the structural features in which the ultrafine fiber aggregates are formed into a bulky structure.

In a normal melt blown process, as plastic resin is discharged from an orifice die and stretched by the high-temperature gas, the diameter of the fiber yarn is determined, which is greatly affected by the properties of the plastic resin itself as well as the discharge pressure, gas temperature, and gas injection speed.

In particular, since the diameter of the fiber yarn varies depending on the use of the nonwoven fabric, it is necessary to adjust the diameter of the fiber yarn according to the conditions in the melt-blown process. Conventionally, in order to confirm the diameter of the fiber yarn, there was only a method of proceeding the melt-blown process to directly confirm the diameter. A method of predicting the diameter prior to proceeding the process was not known.

DETAILED DESCRIPTION OF THE INVENTION

Technical Problem

It is an object of the present invention to provide a method for evaluating physical properties of a melt-blown plastic resin in which, when a particular plastic resin is processed by a melt-blown process, a stretching diameter value after the melt-blown process can be accurately derived from a physical property value measured using a specimen of the resin.

Technical Solution

One aspect of the present invention provides a method for evaluating physical properties of a melt-blown plastic resin including the steps of:
  measuring a molecular weight distribution for a plastic resin specimen;
  deriving a peak molecular weight value from the molecular weight distribution;
  deriving a molecular weight distribution value (Mw/Mn) from the molecular weight distribution; and
  predicting a stretching diameter in a melt-blown process using the peak molecular weight value and the molecular weight distribution value.

Advantageous Effects

According to the present invention, even if a plastic resin is not actually put into the melt-blown process, the diameter of the fiber yarn produced in the melt-blown process can be accurately derived only by the physical properties measured by a specimen, which is thus economical in terms of time and money.

Detailed Description of the Embodiments

The method for evaluating physical properties according to the present invention includes the steps of:
  measuring a molecular weight distribution for a plastic resin specimen;
  deriving a peak molecular weight value from the molecular weight distribution;
  deriving a molecular weight distribution value (Mw/Mn) from the molecular weight distribution; and
  predicting a stretching diameter in a melt-blown process using the peak molecular weight value and the molecular weight distribution value.

The terminology used herein is for the purpose of describing particular exemplary embodiments and is not intended to be necessarily limiting of the present invention. As used herein, the singular forms "a," "an" and "the" are intended to include the plural forms as well, unless the context clearly indicates otherwise. The terms "comprises," "includes" or "have" when used in this specification, specify the presence of stated features, integers, steps, components, or combinations thereof, but do not preclude the presence or addition of one or more other features, integers, steps, components or combinations thereof.

Since the present invention may be modified in various forms, and may have various embodiments, the following exemplary embodiments are illustrated and described in detail. However, this is not intended to limit the present invention to specific embodiments, and the present invention should be construed to encompass various changes, equivalents, and substitutions within the technical scope and spirit of the invention.

Throughout this specification, the plastic resin is a concept including a thermoplastic polymer plastic, and a polymer plastic resin that can be processed into a fiber yarn form by a melt-blown process.

Hereinafter, embodiments of the present invention will be described in detail.

The method for evaluating physical properties of a melt-blown plastic resin according to one aspect of the present invention includes the steps of:
  measuring a molecular weight distribution for a plastic resin specimen;
  deriving a peak molecular weight value from the molecular weight distribution;
  deriving a molecular weight distribution value (Mw/Mn) from the molecular weight distribution; and
  predicting a stretching diameter in a melt-blown process using the peak molecular weight value and the molecular weight distribution value.

The present inventors have made a hypothesis that in the melt-blown molding process of a plastic resin, the stretching diameter of the fiber yarn discharged and processed by the cavity of the orifice is related to the molecular weight characteristics of the plastic resin, and then have found that the stretching diameter of the actual fiber yarn can be accurately derived through specific factors that can be measured from plastic resin specimens, thereby completing the present invention.

Specifically, for the plastic resin specimen, the molecular weight distribution value is measured using a measuring instrument such as GPC (Gel Permeation Chromatography), and a peak molecular weight value and a molecular weight distribution value are derived from the molecular weight distribution, and then from these two values as relevant factors, the stretching diameter value of the fiber yarn can be accurately derived in the melt-blown process.

The peak molecular weight value means a molecular weight value corresponding to the largest peak when the molecular weight distribution of the plastic resin specimen was measured by GPC (Gel Permeation Chromatography)/SEC (Size Exclusion Chromatography), that is, a molecular weight value of the molecule occupying the highest fraction in the plastic resin including molecules having various molecular weight values.

And, since the stretching diameter value of the fiber yarn formed by the melt-blown process is a value that can vary depending on the conditions of the process, the melt-blown process may be performed under the temperature condition of about 150° C. to about 250° C., preferably at a temperature of about 170° C. or about 230° C. However, the present invention is not necessarily limited to the above-mentioned process conditions, and this may vary depending on the melting characteristics of the plastic resin to be processed.

In addition, the stretching diameter value of the fiber yarn formed by the melt-blown process is a value that may vary depending on the stretch ratio in the process. In the melt-blown process, the longitudinal stretch ratio may be about 100 to about 10,000 times, preferably about 100 to about 1,500 times, or about 200 to about 1,200 times.

In this case, the stretching speed may be about 1,000 to about 100,000 times's, preferably about 1000 to about 15,000 times/s, or about 200 to about 1,200 times's.

However, the present invention is not necessarily limited to the above-mentioned process conditions, and the stretching conditions as above may also vary depending on the melting characteristics of the plastic resin to be processed.

Further, the step of predicting the stretching diameter using the peak molecular weight value and the molecular weight distribution value may include a step of deriving a polymer characteristic factor using Mathematical Formula 1 below, and it may include a step of predicting a stretching diameter from this polymer characteristic factor using Mathematical Formula 2 below.

$$\text{Polymer Characteristic Factor} = a(MWD)^b * (Mp)^c \qquad \text{[Mathematical Formula 1]}$$

in Mathematical Formula 1,
MWD is a molecular weight distribution value (Mw/Mn),
Mp is a peak molecular weight value,
a is 0.01 to 0.02,
b is 0.8 to 1.0, and
c is 0.20 to 0.22, $$\text{Predicted Stretching Diameter} = d*(\text{polymer characteristic factor}) - e \qquad \text{[Mathematical Formula 2]}$$

in Mathematical Formula 2,
d is 1.01 to 1.02, and
e is 0.005 to 0.007.

In other words, it is possible to predict the stretching diameter of a fiber yarn formed in a melt-blown process by substituting the molecular weight distribution value and the peak molecular weight value, which are confirmed by measuring the molecular weight distribution, into Mathematical Formula 1 above, introducing the value of each coefficient according to the molecular weight characteristics and melting characteristics of a target plastic resin, then deriving the polymer characteristic factor of the plastic resin according to a simple calculation formula, and then again substituting this factor into Mathematical Formula 2.

More specifically, the value of each coefficient of Mathematical Formulae 1 and 2 may be determined by the steps of measuring the stretching diameter values of a fiber yarn in the actual melt-flown process for some plastic specimens, measuring the above-mentioned MWD value and Mp value, and then substituting the measured values into the functions represented by Mathematical Formulae 1 and 2 to derive the value of each coefficient, and this can be used as a reference.

In particular, the case of Mathematical Formula 1, if log is taken on both sides of the function, it will have the form of simultaneous linear equations with three variables. Thus, even if measured and calculated by taking at least three plastic resin specimens for predicting the stretching diameter of a fiber yarn, accurate coefficient values can be derived, By using these values, the value of each coefficient for various plastic resins can be used as a reference.

In the case of polypropylene resin, in Mathematical Formula 1, a may have a value of about 0.01 to about 0.02, preferably about 0.012 to about 0.015, b may have a value of about 0.8 to about 1.0, preferably about 0.85 to about 0.90, and c may have a value of about 0.2 to about 0.22, preferably about 0.205 to about 0.210.

Further, in Mathematical Formula 2, d may have a value of about 1.01 to about 1.02, preferably about 1.015 to about 1.01, e may have a value of about 0.005 to about 0.007, preferably about 0.006 to 0.0061.

However, the present invention is not necessarily limited to the range of the respective coefficients a to e described above, and respective coefficients may be determined differently according to the molecular weight and melting characteristics of the plastic resin to be measured.

Furthermore, according to one embodiment of the present invention, when the predicted stretching diameter is about 0.35 mm or less, more preferably, when it is about 0.2 to about 0.35 mm, it can be determined to be suitable.

Specifically, the melt-blown process under the above-described conditions may be regarded as a process of forming a fiber yarn for nonwoven fabric production. If the stretching diameter of the fiber yarn in the actual process is too large, the texture of the nonwoven fabric produced is degraded, sound absorption or sound insulation properties may be degraded. If the stretching diameter is too small, it may cause a problem that the mechanical strength of the nonwoven fabric is lowered.

The method for evaluating physical properties according to the present invention as described above is applicable to various plastic polymer resins which are produced in the form of fiber yarn by a melt-blown process.

As an example, the method may be applied to a plastic resin in which the above-mentioned peak molecular weight value is about 10,000 to about 150,000 g/mol, preferably about 30,000 to about 120,000 g/mol.

According to another embodiment of the present invention, the method may be applied to a plastic resin in which the above-described molecular weight distribution value, that is, the ratio (Mw/Mn) of the weight average molecular weight value (Mw) to the number average molecular weight value (Mn) is about 4 or less, preferably about 1 to 4, more preferably about 2 to about 3.5.

Further, the method may be applied to a plastic resin in which the number average molecular weight value is about 10,000 to about 50,000 g/mol, preferably about 20,000 to about 45,000 g/mol. The weight average molecular weight value of such plastic resin may be preferably about 10,000 to about 200,000 g/mol, preferably about 50,000 to about 140,000 g/mol.

And specifically, polystyrene-based resin, polyolefin-based resin, polyvinyl chloride-based resin, poly (meth) acrylic-based resin, polyamide-based resin, ABS-based resin, urethane epoxy-based resin, urethane acrylic-based resin, amino resin, phenol resin, and polyester-based resin are subjected to a melt-blown molding process to form a fiber yarn, and such fiber yarn can be applied for various plastic resins that are processed into products, but when it, is applied for a thermoplastic resin, more accurate evaluation results can be presented. Among them, it may be preferably applied to a polyolefin-based resin such as polyethylene and polypropylene resin, among which polypropylene-based resin is most preferred.

Hereinafter, the functions and effects of the present invention will be described in more detail with reference to examples. However, these examples are given for illustrative purposes only and are not intended to limit the scope of the present invention.

EXAMPLE

Preparation of Plastic Resin Specimen

The polypropylene resin having physical property values shown in Table 1 below was dried in a vacuum oven at 40° C. overnight to prepare in the form of pellets using a twin screw extruder (BA-19, manufacturer BAUTECH).

The resin in the form of pellets obtained by compression was again dried in a vacuum oven at 40° C. overnight, and then a specimen was prepared in a form suitable for the measurement conditions of each physical property using a specimen manufacturing machine (Xplore 5.cc micro injection molding machine).

1) Measurement of Molecular Weight Characteristics

Molecular weight characteristics of the prepared specimens were measured via GPC/SEC. Tice number average molecular weight, the weight average molecular weight, the molecular weight distribution value, and the peak molecular weight value were simultaneously measured.

The peak molecular weight value and the molecular weight distribution value were substituted into the following Mathematical Formulas to predict the stretching diameter value of the fiber yarn after the melt-blown process.

$$\text{Polymer Characteristic Factor} = a \cdot (MWD)^b \cdot (Mp)^c \quad \text{[Mathematical Formula 1]}$$

$$\text{Predicted Stretching Diameter} = d \cdot (\text{Polymer Characteristic Factor}) - e \quad \text{[Mathematical Formula 2]}$$

In Mathematical Formula, each coefficient is a value corresponding to polypropylene, and a=0.01463, b=0.8854, c=0.2066, d=1.01687, and e=0.00607, respectively, 2) Measurement of Stretching Diameter of Fiber Yarn For accurate stretching diameter measurement, a DHR (Discovery Hybrid Rheometer) from TA Instruments used for measurement of flow properties of the fluid was used.

The prepared polypropylene pellet (PP) was melted and loaded between the upper and lower plates of the DHR. (conditions of temperature: 170° C., initial diameter of PP loaded between upper and lower plates: 8 mm, initial thickness: 1.5 mm).

The molten PP, which was loaded between the upper and lower plates, was stretched while the upper plate of the DHR was raised to a stretching speed of 10 minis which was taken with an ultrafast camera (IDT's CrashCam 1520), and the diameter of the stretched PP was measured through image analysis (analysis tool: ImageJ).

The molecular weight-related measured values are summarized in Table 1 below. Polymer characteristic factors, predicted diameter values, and measured diameter values derived therefrom are summarized in Table 2 below.

TABLE 1

|  | Number average molecular weight (g/mol) | Weight average molecular weight (g/mol) | Molecular weight distribution (Mw/Mn) | Peak molecular weight (g/mol) |
| --- | --- | --- | --- | --- |
| Example 1 | 22055 | 52625 | 2.39 | 40,371 |
| Example 2 | 40385 | 93264 | 2.31 | 72,898 |
| Example 3 | 35326 | 90003 | 2.55 | 83,935 |
| Example 4 | 26605 | 57806 | 2.17 | 55,674 |
| Example 5 | 22156 | 49442 | 2.23 | 45,953 |
| Example 6 | 23764 | 54845 | 2.20 | 56,638 |
| Example 7 | 25328 | 57571 | 2.27 | 58,453 |
| Example 8 | 39255 | 137899 | 3.51 | 104,164 |
| Example 9 | 42560 | 128591 | 3.02 | 96,022 |
| Example 10 | 42326 | 134202 | 3.17 | 105,590 |
| Example 11 | 44496 | 131242 | 2.95 | 102,759 |

TABLE 2

| | Stretch ratio (times) | Polymer characteristic factor | Predicted diameter value (mm) | Measured diameter value (mm) |
|---|---|---|---|---|
| Example 1 | 1093 | 0.283 | 0.282 | 0.242 |
| Example 2 | 756 | 0.310 | 0.309 | 0.291 |
| Example 3 | 425 | 0.349 | 0.349 | 0.388 |
| Example 4 | 954 | 0.278 | 0.276 | 0.259 |
| Example 5 | 1093 | 0.273 | 0.272 | 0.242 |
| Example 6 | 761 | 0.282 | 0.281 | 0.290 |
| Example 7 | 653 | 0.292 | 0.291 | 0.313 |
| Example 8 | 284 | 0.484 | 0.486 | 0.475 |
| Example 9 | 359 | 0.417 | 0.417 | 0.422 |
| Example 10 | 337 | 0.443 | 0.445 | 0.436 |
| Example 11 | 443 | 0.414 | 0.415 | 0.380 |

Referring to Table 2 above, it can be clearly seen that the tensile diameter of the fiber yarn predicted according to one example of the present invention has a value very similar to that of the fiber yarn measured in the actual process.

In particular, when the actual diameter value and the predicted diameter value are compared and verified, the Pearson correlation coefficient value appears to reach about 0.92, confirming that it has a very high correlation. Although respective stretch ratios are different when stretched at the same speed, it can be confirmed that the correlation between the actual value and the predicted value is very high. This can be seen as clearly e explaining that the actual tensile diameter value of the plastic resin fiber yarn is directly related to the above-described molecular weight distribution value and peak molecular weight value.

When the actual tensile diameter value of the plastic resin fiber yarn is not directly related to the above-mentioned molecular weight distribution value or peak molecular weight value, irrespective of each coefficient value in Mathematical Formulae 1 and 2 above, the predicted tensile diameter value cannot converge to the actual tensile diameter value.

However, the actual tensile diameter value of the plastic resin fiber yarn is clearly verified as having a first order correlation with the value predicted by Mathematical Formulae 1 and 2. This can be said to be the result clearly supporting that as shown in the present invention, in the melt-blown process of the plastic resin, the tensile diameter value of the fiber yarn has a direct correlation with the molecular weight characteristic of each plastic resin, regardless of each coefficient value used in Mathematical Formulae 1 and 2.

The invention claimed is:

1. A method for producing a nonwoven fabric, comprising:
    preparing a plastic resin in a dried pellet form,
    measuring a molecular weight distribution of the prepared plastic resin;
    deriving a peak molecular weight value from the molecular weight distribution of the prepared plastic resin;
    deriving a molecular weight distribution value (Mw/Mn) from the molecular weight distribution of the prepared plastic resin; and
    calculating a predicted stretching diameter of a nonwoven fabric produced by the prepared plastic resin through a melt-blown process by using Mathematical Formulas 1-2, $$\text{Polymer Characteristic Factor} = a(MWD)^b * (Mp)^c \qquad \text{[Mathematical Formula 1]}$$

in Mathematical Formula 1,
    MWD is the molecular weight distribution value (Mw/Mn) of the prepared plastic resin,
    Mp is the peak molecular weight value of the prepared plastic resin,
    a is 0.01 to 0.02,
    b is 0.8 to 1.0, and
    c is 0.20 to 0.22, $$\text{Predicted Stretching Diameter} = d*(\text{Polymer Characteristic Factor}) - e \qquad \text{[Mathematical Formula 2]}$$

in Mathematical Formula 2,
    d is 1.01 to 1.02, and
    e is 0.005 to 0.007, and
    producing a nonwoven fabric by melt-blowing the prepared plastic resin which has the predicted stretching diameter of about 0.35 mm or less.

2. The method according to claim 1, wherein
when the molecular weight distribution of the prepared plastic resin is measured by GPC/SEC, the peak molecular weight value of the prepared plastic resin is a molecular weight value corresponding to a largest peak.

3. The method according to claim 1, wherein
the melt-blown process is performed under the temperature condition of 150° C. to 250° C.

4. The method according to claim 1, wherein the melt-blown process is performed at a longitudinal stretch ratio of 100 times to 10,000 times.

5. The method according to claim 1, wherein the peak molecular weight value of the prepared plastic resin is 10,000 g/mol to 150,000 g/viol.

6. The method according to claim 1, wherein the molecular weight distribution value (Mw/Mn) of the prepared plastic resin is 4 or less.

7. The method according to claim 1, wherein the plastic resin has a number average molecular weight value (Mn) of 10,000 g/mol to 50,000 g/mol.

8. The method according to claim 1, wherein
the plastic resin has a weight average molecular weight value (Mw) of 10,000 g/mmol to 200,000 g/mol.

9. The method according to claim 1, wherein the plastic resin is a polypropylene resin.

* * * * *